United States Patent
Heldman et al.

(10) Patent No.: US 11,918,810 B1
(45) Date of Patent: *Mar. 5, 2024

(54) METHOD AND SYSTEM FOR TUNING OF MOVEMENT DISORDER THERAPY DEVICES

(71) Applicant: Great Lakes NeuroTechnologies Inc., Cleveland, OH (US)

(72) Inventors: Dustin A. Heldman, Shaker Heights, OH (US); Joseph P. Giuffrida, Hinckley, OH (US); Thomas O. Mera, Columbus, OH (US)

(73) Assignee: Great Lakes Neurotechnologies Inc., Cleveland, OH (US)

( * ) Notice: Subject to any disclaimer, the term of this patent is extended or adjusted under 35 U.S.C. 154(b) by 152 days.

This patent is subject to a terminal disclaimer.

(21) Appl. No.: 17/487,038

(22) Filed: Sep. 28, 2021

Related U.S. Application Data

(63) Continuation of application No. 15/494,930, filed on Apr. 24, 2017, now Pat. No. 11,160,979, which is a continuation of application No. 13/153,063, filed on Jun. 3, 2011, now Pat. No. 9,662,502, which is a continuation-in-part of application No. 12/818,819, filed on Jun. 18, 2010, now abandoned, and a
(Continued)

(51) Int. Cl.
*A61N 1/36* (2006.01)
*A61N 1/372* (2006.01)

(52) U.S. Cl.
CPC ..... *A61N 1/36067* (2013.01); *A61N 1/36139* (2013.01); *A61N 1/37217* (2013.01); *A61N 1/37247* (2013.01)

(58) Field of Classification Search
None
See application file for complete search history.

(56) References Cited

U.S. PATENT DOCUMENTS

| | | | | |
|---|---|---|---|---|
| 8,187,209 | B1 * | 5/2012 | Giuffrida | A61M 5/1723 600/595 |
| 8,391,986 | B2 * | 3/2013 | Graupe | A61B 5/296 607/45 |
| 9,662,502 | B2 * | 5/2017 | Giuffrida | A61N 1/36135 |

(Continued)

*Primary Examiner* — Robert A Sorey
(74) *Attorney, Agent, or Firm* — Brian Kolkowski

(57) ABSTRACT

A system and method for tuning the parameters of a therapeutic medical device comprises a movement measurement data acquisition system capable of wireless transmission; processing comprising kinematic feature extraction, a scoring algorithm trained using scores from expert clinicians, a therapeutic device parameter setting adjustment suggestion algorithm preferably trained using the parameter setting adjustment judgments of expert clinicians; and a display and/or means of updating the parameter settings of the treatment device. The invention facilitates the treatment of movement disorders including Parkinson's disease, essential tremor and the like by optimizing deep brain stimulation (DBS) parameter settings, eliminating as much as possible motor symptoms and reducing time and costs of surgical and outpatient procedures and improving patient outcomes. In preferred embodiments, the system provides recommendations for treatment which may be semi-automatically or automatically applied to update the parameter settings of a treatment device such as a DBS implant.

20 Claims, 5 Drawing Sheets

Related U.S. Application Data continuation-in-part of application No. 12/250,792, filed on Oct. 14, 2008, now abandoned.

(56) References Cited

U.S. PATENT DOCUMENTS

| | | | | |
|---|---|---|---|---|
| 2004/0088025 | A1* | 5/2004 | Gesotti | A61N 1/36003 607/49 |
| 2004/0249422 | A1* | 12/2004 | Gliner | A61N 1/0534 607/45 |
| 2005/0234309 | A1* | 10/2005 | Klapper | A61B 5/6828 600/300 |
| 2006/0058855 | A1* | 3/2006 | Gill | A61N 1/0539 607/45 |
| 2007/0055322 | A1* | 3/2007 | Forsberg | G16H 50/50 607/59 |
| 2007/0118044 | A1* | 5/2007 | Remes | A61B 5/4824 128/905 |
| 2007/0179534 | A1* | 8/2007 | Firlik | A61M 5/14276 604/503 |
| 2008/0208288 | A1* | 8/2008 | Gesotti | A61N 1/36003 607/48 |
| 2008/0281376 | A1* | 11/2008 | Gerber | A61N 1/36082 607/48 |
| 2008/0288023 | A1* | 11/2008 | John | G16H 20/40 607/59 |
| 2008/0312513 | A1* | 12/2008 | Simon | A61B 5/165 600/300 |
| 2013/0123684 | A1* | 5/2013 | Giuffrida | A61B 5/7405 607/45 |

* cited by examiner

METHOD AND SYSTEM FOR TUNING OF MOVEMENT DISORDER THERAPY DEVICES

CROSS-REFERENCE TO RELATED APPLICATIONS

This application is a continuation of U.S. patent application Ser. No. 15/494,930, which was filed on Apr. 24, 2017, issued as U.S. Pat. No. 11,160,979 on Nov. 2, 2021, and which is a continuation of U.S. patent application Ser. No. 13/153,063, which was filed on Jun. 3, 2011, issued as U.S. Pat. No. 9,662,502 on May 30, 2017, and which is a continuation-in-part of both 1) U.S. patent Application Ser. No. 12/818,819, which was filed on Jun. 18, 2010, and 2) U.S. patent application Ser. No. 12/250,792, which was filed on Oct. 14, 2008. The specifications and drawings of each of the above patents and applications are hereby incorporated by reference in their entirety.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of grant number 1R44AG033520 awarded by the National Institutes of Health, National Institute on Aging.

BACKGROUND OF THE INVENTION

(1) Field of the Invention

The present invention relates to therapeutic medical apparatus, systems, devices and/or methods, and more particularly, to apparatus and methods for using neural stimulation to alleviate the symptoms of movement disorders, such as those associated with Parkinson's disease, essential tremor, dystonia, and Tourette's syndrome, including tremor, bradykinesia, rigidity, gait/balance disturbances, and dyskinesia.

(2) Technology Review

A current trend in the treatment of diseases identified as being associated with the central nervous system is the stimulation of target areas of the central nervous system to effect therapeutic benefit. Such stimulation has been accomplished with, for example, implanted electrodes that deliver electrical stimulation to target brain regions; one class of electrical neural stimulation devices has been categorized under the name "deep brain stimulation" (DBS). Although the exact neurological mechanisms by which DBS therapies succeed are complex and are not yet fully understood, such therapies have proven effective in treating Parkinson's disease motor symptoms (such as tremor, bradykinesia, rigidity, and gait disturbances), and investigation into the use of DBS for the treatment of this and other neurological and mental health disorders, including major depression, obsessive-compulsive disorder, tinnitus, obesity, criminal tendencies, and antisocial disorders, is ongoing.

Typically, medication for Parkinson's disease (PD) consists of Levodopa to alleviate symptoms. Over time, however, the medication has reduced efficacy and shows increased occurrence of side effects such as dyskinesias. Once side effects outweigh benefits, patients consider deep brain stimulation (DBS). An electrode/wire lead is implanted in a specific location in the brain which shows hyperactivity in PD patients and is sensitive to electrical stimulation. PD target sites are the subthalamic nucleus (STN) or globus pallidus internus (GPi). The Essential tremor and Parkinson tremor target site is generally the ventral *intermedius* nucleus of the thalamus (VIM). Electrical pulses characterized by amplitude (volts), current (amps), frequency (Hz), and pulse width (microseconds) are regulated by an implantable pulse generator (IPG) placed beneath the skin on the chest. Stimulation affects motor symptoms on the contralateral side, i.e., right side tremor will be treated on the left brain. After a patient has been implanted and recovered, programming sessions will fine tune stimulation settings described above in order to minimize symptom severity, minimize side effects, and maximize IPG battery life span. Although medication is not eliminated, it is typically reduced significantly. DBS efficacy decreases over time as the body adjusts to stimulation and protein buildup around electrode lead attenuates electrical field. Programming sessions are required throughout the patient's lifetime, though the frequency of adjustments are typically greater at first.

A typical implanted DBS stimulation lead consists of a thin insulated needle comprising four platinum/iridium electrodes spaced 0.5 or 1.5 mm apart along the length of the lead. One or multiple leads may be implanted in a target brain region or regions to provide symptom-inhibiting high-frequency stimulation, although some research suggests that excellent results can be achieved even when the lead is implanted distant from a target region. A DBS lead is connected to an implantable pulse generator (IPG), which serves as a controller and power source, via an extension cable tunneled subcutaneously to a subcutaneous pocket in the chest or abdominal cavity. The IPG typically includes a battery and circuitry for telemetered communication with an external programming device used to adjust, or "tune," DBS lead stimulation parameters, which may include stimulation frequency, amplitude, pulse width (or wavelength), and contact configuration (that is, the selection of which electrodes are utilized from among the four electrodes available on a lead, and, if two or more electrodes are active, the relative polarity of each). These parameters are initially set during implantation surgery and are then further fined-tuned in the outpatient clinic or in a doctor's office following surgery to maximize therapeutic benefit and minimize undesirable stimulation-induced side effects. The first such tuning session usually takes place several weeks following implantation surgery, after the patient has recovered and inflammation at the lead placement site has subsided.

While the above-described equipment and procedures are typical as of the filing of this application, variations and refinements may become commonplace as neural implant technology advances. Conceivably, uses of a multiplicity of DBS leads or networks of DBS leads may provide greater coverage, enabling the stimulation of larger and more varied target areas, and miniaturization and improved telemetry may obviate the need for the extension cable and/or the IPG altogether as leads become self-powering and/or self-controlling or permit for built-in telemetry. Advances in nanotechnology and materials may also allow DBS leads in the future to become self-repositioning, self-cleaning, or resistant to biological rejection for improved long-term therapeutic operation and more precisely targeted implantation.

The current standard in evaluating the severity of movement disorder symptoms in Parkinson's disease is the Unified Parkinson's Disease Rating Scale (UPDRS) used to score motor tests, many of which involve repetitive movement tasks such as touching the nose and drawing the hand away repeatedly, or rapidly tapping the fingers together. A battery of exercises, typically a subset of the upper extremity motor section of the UPDRS, is normally completed during DBS lead placement surgery and subsequent programming sessions to evaluate performance while a clinician qualitatively assesses symptoms. Each test is evaluated by a clinician based solely on visual observation and graded on a scale that ranges from 0 (insevere) to 4 (severe).

During DBS implantation surgery, various lead placement strategies are used, including inversion recovery imaging, reformatted anatomical atlases, and formula coordinates based on known landmarks. Implantation location is verified and adjusted based on electrophysiological mapping using techniques such as microelectrode recording and micro and macro stimulation. Currently, lead placement and stimulation parameters are modified based on subjective motor examinations such as clinical observation such as the UPDRS motor tasks during the implantation procedure. After lead placement, patient motor symptoms are evaluated in response to a set of stimulation parameters. Stimulation parameters are then adjusted, and motor exam repeated. This trial-and-error process of adjusting parameters and monitoring patient response is continued until an optimal electrode position and stimulation set are established. During this programming or "tuning" process, the clinician subjectively assesses motor symptom improvement.

Postoperatively, assessing DBS response and reprogramming stimulation parameters require a significant time commitment. Several stimulation parameters can be modified, including electrode polarity, amplitude, current, pulse width, and frequency. DBS programming and patient assessment may be performed by a variety of healthcare professionals, including movement disorder neurologists, neurosurgeons, fellows, occupational and physical therapists, and nurses. Stimulation optimization must be performed based on results of an exam such as the UPDRS, with the patient in four states (off medication/off DBS, off medication/on DBS, on medication/off DBS, and on medication/on DBS) per the Core Assessment Program for Surgical Intervention Therapies in Parkinson's disease (CAPSIT-PD) protocol. The process of DBS adjustment is iterative and largely involves trial-and-error. Retrospective studies have found that DBS programming sessions take more than twice as long as typical evaluations by movement disorder neurologists. Programming sessions are typically limited to 1-3 hours since longer sessions result in patient fatigue or lightheadedness. Programming and patient assessment from preoperatively to one year after surgery requires approximately 30 hours of nursing time per patient.

Clinicians presently lack tools that combine physiological, electrical, and behavioral data to optimize electrode placement and stimulator programming. Optimizing electrode placement and stimulation parameters improves patient outcome by alleviating motor symptoms and minimizing complications. The present invention addresses this need for improved electrode placement and adjustment of deep brain stimulation parameters by providing a repeatable, automated or semi-automated tool that can assist stimulation parameter tuning during surgical electrode placement and outpatient programming sessions. In particular, the present invention aims to provide methods for the collection and transmission of objective biokinetic data during these procedures, which data is then processed to output objective movement disorder symptom severity measures on a continuous scale in real-time to guide clinician decision making. The improved resolution and repeatable results of the present invention should reduce time and costs of DBS procedures as well as improve patient outcomes.

It is therefore the object of the present invention to couple automatically-assigned quantitative motor assessments with procedures and practices for DBS implantation and parameter tuning in semi-automatic and automatic ways to provide improved and less costly movement disorder patient therapy.

Existing systems for quantifying Parkinson's disease motor symptoms are described in this application's parent application, U.S. patent application Ser. No. 12/250,792, which is herein incorporated by reference, and which describes a novel system for measuring motor dysfunction symptoms and computing measures based on UPDRS scores therefrom. Preferably, the system and methods described therein are incorporated, in whole or in part, into the present invention as a means of automatic symptom quantification. The resultant scores objectively quantify movement disorder symptoms advantageously using a scale that is familiar to clinicians.

SUMMARY OF THE INVENTION

The present invention relates to methods for automatically and semi-automatically adjusting treatment parameters in therapy systems. The present invention further provides methods of quantifying movement disorders for the treatment of patients who exhibit movement disorder symptoms such as may be caused by Parkinson's disease. The present invention further relates to a symptom quantification algorithm trained using reference data, particularly where the data comprises clinician-assigned movement disorder test scores given on the Unified Parkinson's Disease Rating Scale, and more particularly when the scores are given for tests from the UPDRS motor examination. The present invention further relates to a therapeutic device parameter adjustment algorithm, particularly where the algorithm is trained using reference data, and more particularly where the data comprises clinician-assigned therapeutic device parameter adjustments and which data therefore represents the judgment of one or more expert clinicians.

Objective quantification of a subject's movement disorder symptoms, including tremor, bradykinesia, dyskinesia, and gait/balance disturbances requires, as a first step, a measurement of the movement. This measurement can be performed by measuring a single parameter or different parameters; the parameter or parameters being measured may include linear or rotational displacement, velocity, or acceleration, electromyographic (EMG) signals, or any other parameter that could give a quantitative indication of motion; and the part of the body being measured for motion may be a limb (as at a wrist, ankle, or finger) or may be the trunk of the body (as at a shoulder or torso) and by other techniques known to those skilled in the art. Sensors used for measuring body motion include gyroscopes and accelerometers, preferably miniaturized; electromagnets; EMG; video; or other sensors known to those skilled in the art. Other systems that can be used to detect and measure body motion include motion capture systems, machine vision systems, sonic or laser Doppler velocity transducers, infrared systems, GPS, or any other system known to those skilled in the art. The movement data acquisition system, or "movement measuring apparatus," used in the present invention may incorporate one or more of any of the above sensors or systems. A pre-existing movement data acquisition system, such as the one described in patent application Ser. No. 11/082,668, herein incorporated by reference, may similarly be used. In the present disclosure, "movement data" is construed as including, but not being limited to, any signal or set of signals, analog or digital, corresponding to movement of any part of the body or multiple parts of the body, independently or in conjunction with each other. Movement may be continuously measured over long time spans, or may be measured only over a short time span, for example, during the period of only one or several tests taken from or modified from the UPDRS motor exam. In certain embodiments of the present invention, the measurement time needed to produce a score substantially predictive of a UPDRS score for a given test on the UPDRS motor exam is acquired during a test lasting no more than about 20 seconds. Further, in certain embodiments of the present invention, the measurement time needed to produce scores substantially predictive of a set of multiple UPDRS scores for multiple given tests on the UPDRS motor exam is acquired during a test preferably lasting no more than about 30 minutes. More preferably, the measurement time does not exceed minutes. More preferably, the measurement time does not exceed 10 minutes. Even more preferably, the measurement time does not exceed 5 minutes. Even still more preferably, the measurement time does not exceed 3 minutes. Still more preferably, the measurement time does not exceed 1 minute. Still more preferably, the measurement time does not exceed 30 seconds. Most preferably, the measurement time does not exceed 15 seconds.

Following measurement of symptomatic movement, the next step in objective quantification of a subject's movement disorder symptoms is the extraction of statistical kinematic features from the acquired movement data via processing. This processing may take place during or following data acquisition and may occur within a movement data acquisition device or within a different processing device, such as a personal computer, PDA, smart phone, tablet PC, touch screen interface, or the like, with which the acquisition device interfaces, either through a cable connection or by wireless transmission. Useful kinematic features that may be extracted from gyroscopic data may include, for example, peak power angular velocity, peak power angle, RMS angular velocity, frequency, maximum amplitude, maximum peak-to-peak amplitude, mean angular velocity, and wavelet parameters, as well as the covariance or standard deviation over time of any of these parameters. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance or standard deviation over time of any of these parameters. In a movement data acquisition system, or movement measuring apparatus, that combines a three-axis accelerometer and a three-axis gyroscope to produce 6 channels of movement data, one or any combination of the above kinematic features can be extracted from any of the 6 kinematic channels to be used as inputs to a trained algorithm in the next step. The listed kinematic features for the sensors above are intended to be exemplary, and not limiting; other types of sensors will produce different data from which different sets of features may be extracted.

The trained algorithm used to process the kinematic features extracted from the movement data may comprise, for example, one or more of a simple or multiple linear regression, an artificial neural network, a Bayesian network, or a genetic algorithm. The output of the trained algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that involve recommendations for treatment or closed-loop automated treatment delivery.

Following the step of symptom quantification, a separate algorithm computes suggested changes to the therapy system parameter settings based on the result of the symptom quantification algorithm and known or predicted current therapy system parameter settings physiological models.

Depending on the embodiment of the invention, the current therapy system parameter settings changes may be input into the algorithm by a human user such as a clinician using a hardware or software user interface, or may be automatically sensed from the DBS parameter settings by communicating with a DBS implant or its programmer device, or may be known because the DBS parameter settings have been reset to some known baseline settings or restored to a previously saved settings preset. The existing parameter settings might also be predicted or derived based, for example, on observed or measured therapy effectiveness.

Suggested therapy system parameter settings changes are then input into the therapy system, and their effectiveness is measured using the above-described method of symptom quantification.

The process of therapy system parameter settings adjustment may remain iterative, but the invention greatly reduces the time and expertise required to arrive at optimized stimulation parameter settings, advantageously allowing clinicians with lesser training or experience to adjust parameter settings during patient visits, and to do so in less time than is currently required. Additionally, the present invention increases access to geographically disparate populations by putting the expertise into the system and reducing or eliminating the need for an expert or trained clinician to be present with each subject.

A number of embodiments of the present invention are envisioned in this disclosure. These embodiments are examples of the many embodiments encompassed by the present invention, but do not in any way limit the many other embodiments covered by this disclosure.

In one embodiment, the method for adjusting brain stimulation electrodes in a subject for treating a subject's movement disorder comprises the steps of applying at least one sensor having a signal to a post-surgical subject having an implanted brain stimulation device for treatment of a movement disorder; quantifying at least one symptom of the subject's movement disorder with the signal from the at least one sensor using a processor; outputting the quantification of the at least one symptom to a display; and adjusting the implanted brain stimulation device for treatment of the movement disorder based at least in part on the outputted quantification of the at least one symptom. In an embodiment designed to assist in optimizing therapy for movement disorders in the extremities, preferably at least two sensors are applied to a finger of the post-surgical subject, and the sensors include both an accelerometer and a gyroscope. More preferably, the sensors are packaged in an enclosure weighing altogether no more than about 12 grams and no larger than about 12 cubic centimeters. Preferably, the movement disorder symptom quantification is based on historical data, which is preferably UPDRS scores assigned to movement disorder patients by one or more expert clinicians. Preferably, the therapy parameter adjustment is based at least in part on historical data, which preferably comprises recorded adjustments made to brain stimulation devices implanted in movement disorder patients, the adjustments having been made by at least one expert clinician, and preferably multiple expert clinicians.

In another embodiment, the method for adjusting treatment parameters of a therapeutic medical device in a subject comprises the steps of applying at least one sensor having a signal to a subject presently using a therapeutic medical device for treatment of a disorder, the therapeutic medical device having more than two adjustable parameters; measuring at least one symptom of the subject's disorder with the signal from the at least one sensor; selecting at least one parameter of the therapeutic medical device to adjust; estimating or calculating a level of adjustment to be applied to the selected at least one parameter of the therapeutic medical device using a processor, the estimation or calculation being based at least in part on the measurement of the at least one symptom and at least in part on recorded data representing the judgment of one or more expert clinicians; presenting the estimated or calculated level of adjustment for the selected at least one parameter of the therapeutic medical device to a medical professional and/or the subject; and adjusting the at least one parameter of the therapeutic medical device based at least in part on the estimated or calculated level of adjustment to be made. Preferably, the level of adjustment for the selected at least one parameter of the therapeutic medical device is estimated or calculated using an artificial neural network trained using recorded data representing the judgment of one or more expert clinicians; preferably, this recorded data comprises parameter settings adjustments made to like therapy devices for multiple patients. The therapeutic device may be any of a number of devices, including stimulation implants such as DBS implants or drug delivery systems such as those that comprise a drug delivery pump and a drug reservoir. Preferably, the step of adjusting the at least one parameter of the therapeutic medical device is executed upon the manual or vocal confirmation of the presented estimated or calculated level of adjustment, the confirmation being made by a medical professional or the subject. In other embodiments, the step of adjusting the at least one parameter of the therapeutic medical device is carried out by a closed loop control system, which automatically adjusts the settings based at least in part on the estimated or calculated level of adjustment.

Yet another embodiment of the present invention is a system for adjusting the parameters of a deep brain stimulation device implanted in a subject for treating a subject's movement disorder by a clinician after surgery, the system comprising a sensor unit comprising an accelerometer and/or gyroscope, the sensor unit being protected by an enclosure and the sensor unit having an analog signal related to the movement of a subject with a movement disorder, the subject having a deep brain stimulation implant having adjustable parameters; an electronic module for receiving the analog signal acquired by the sensor unit, the electronic module comprising a memory and an analog-to-digital converter for converting the analog signal into a digital signal; a processing module for receiving the digital signal and for processing the signal acquired by the sensor unit, for receiving an input related to the subject's deep brain stimulation implant's parameter settings during measurement of the analog signal with the sensor unit, and to produce an output comprising computed adjustments for one or more of the adjustable parameters of the deep brain stimulation implant, the output being based at least in part on the signal acquired by the sensor; and a display for receiving the output.

Preferably, the movement measuring apparatus is small, lightweight, and not cumbersome. In some embodiments of the present invention, the movement measuring apparatus preferably consists only of one or two sensor packages placed only on the wrist and a finger of the subject and has a mass of no more than about 12 grams. More preferably, the movement measuring apparatus consists of a sensor package placed only on the finger of the subject and weighs no more than half an ounce. Even more preferably, in other embodiments, the movement measuring apparatus is machine vision-based and uses a video camera or similar sensor to detect the motion of the subject without any sensor devices placed on the body of the subject.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DETAILED DESCRIPTION OF THE INVENTION

The present invention relates to the programming of therapeutic medical devices having parameters, and methods and systems for automatically and semi-automatically adjusting those parameters. In embodiments of the invention which relate to deep brain stimulation (DBS) implant parameter settings adjustment for the treatment of movement disorder symptoms, the invention includes a method of objectively quantifying the severity of a subject's movement disorder and a method of deriving optimized parameter settings. The symptom quantification may be reduced to a simple score on a scale equivalent to that of the Unified Parkinson's Disease Ratings Scale (UPDRS). The present invention provides a repeatable, automated tool that can assist stimulation tuning during surgical electrode placement and outpatient follow-up, thus optimizing patient outcomes and reducing associated time and costs without adding excessive burden to subjects or clinicians.

The systems and methods of the various embodiments of the present invention are used to analyze, score, and treat various disorders, and especially movement disorders. Movement disorders for purposes of this application include but are not limited to Parkinson's disease and essential tremor. Some of the treatments used for these disorders involve pharmaceutical interventions, fetal cell transplants, surgery, or deep brain stimulation. The efficacy of an intervention is often judged by the intervention's ability to alleviate subject symptoms and improve subject quality of life. The subject on which the system or method is used is a human or another form of animal.

The present invention includes a trained algorithm to determine scoring from movement data acquired by a movement measuring apparatus. The trained algorithm in part comprises a mathematical model or quantitative representation, used to process kinematic features computed from the movement data and may include some of those steps known to those skilled in the art. In some embodiments of the present invention, the scoring may done on a continuously variable scale of 0-4 with scores substantially similar to or predictive of scores that would be given on the Unified Parkinson's Disease Ratings Scale by an expert clinician. ("Expert clinician" for the purposes of this application is taken to mean a doctor, nurse, researcher, or other medical or scientific professional trained for and experienced in the task of interest, e.g., motor function assessment using the UPDRS, or DBS programming.)

The Applicants herein incorporate the following U.S. Pat. Nos. by reference: 11/082,668 filed Mar. 17, 2005; Ser. No. 11/432,583 filed May 11, 2006; Ser. No. 12/250,792 filed Oct. 14, 2008; and Ser. No. 12/818,819 filed Jun. 18, 2010.

Figure 1:
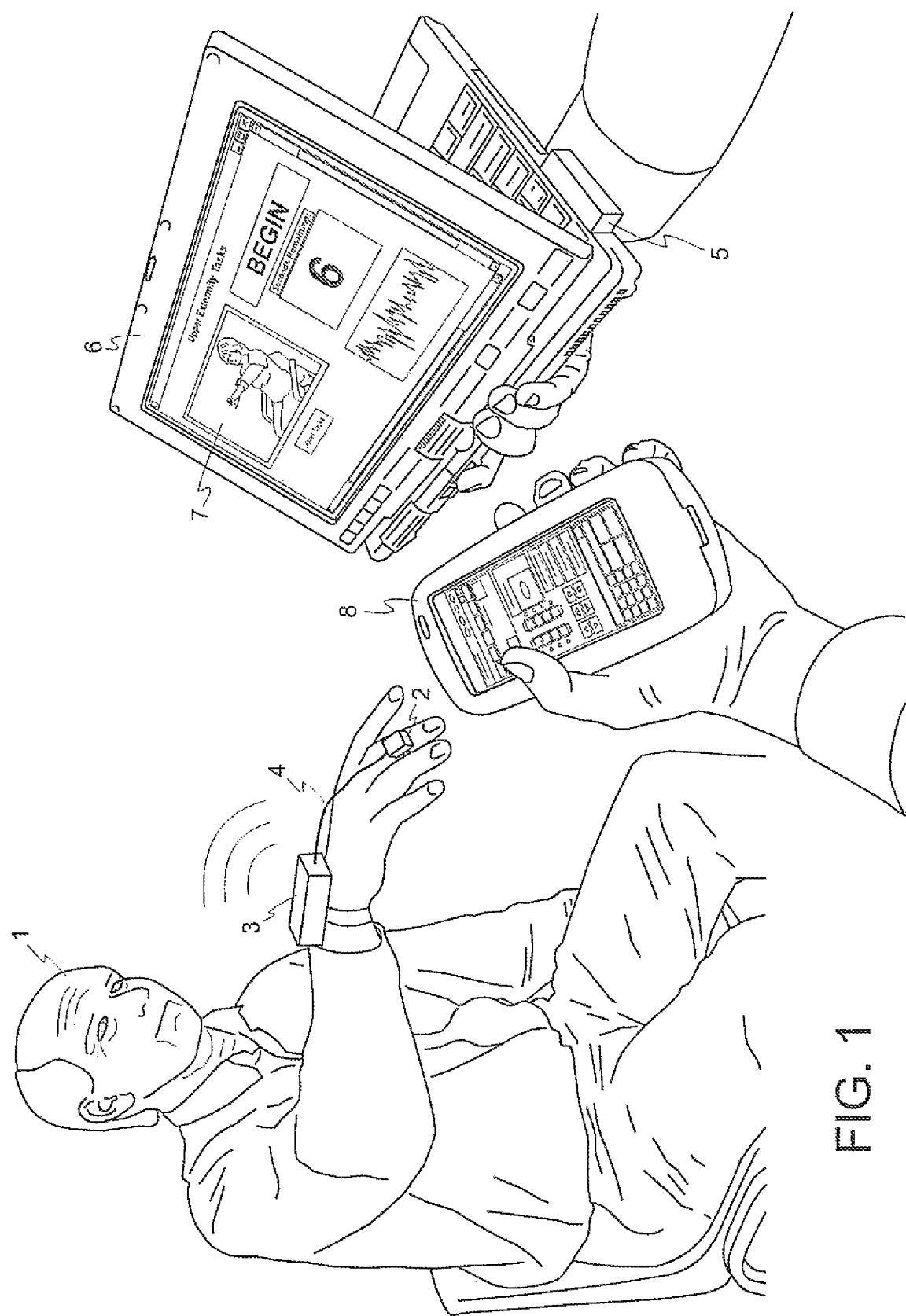
FIG. 1. Schematic view of a subject undergoing post-surgical DBS adjustment with one embodiment of the invention.

FIG. 1 illustrates the therapeutic device programming (or "tuning," or "parameter settings adjustment") process with one embodiment of the invention. A subject 1 has a therapy device (not shown), which in the illustrated case is a therapy device for the treatment of a movement disorder, such as a DBS implant. Subject 1 wears a sensor unit 2 comprising accelerometers and/or gyroscopes (both not shown) as well as a transmission system (not shown). Preferably, the sensor unit 2 comprises three orthogonal accelerometers and three orthogonal gyroscopes. Preferably, these are micro-electrical-mechanical (MEMS) accelerometers or gyroscopes, such as Analog Devices ADXL210 accelerometers and Analog Devices ADXRS300 gyroscopes. The transmission system may be wired or wireless, and may communicate via any medium and any transmission protocol known to those skilled in the art. In the illustrated embodiment, the sensor unit 2 communicates sensor readings to a command module 3 over a small flexible transmission cable 4, though this transmission could also be conducted wirelessly. In the illustrated embodiment, the sensor unit 2 is worn on the middle phalange of the middle finger and the command module 3 is worn on the wrist using a wristband, though the placement of the sensor unit 2 and command module 3 may vary depending upon the symptoms of the movement disorder; alternate placements could include the ankle, foot, shoulder, or elsewhere on the trunk of the body or on any part of any extremity. While the illustrated embodiment shows the sensor unit 2 and the command module 3 as having separate enclosures, permitting for a lighter-weight sensor unit 2 that is easily worn on the finger, in alternate embodiments the sensor unit 2 and command module 3 may be integrated into a single enclosure.

The command module 3 supplies power to the sensor unit 2, stores data in memory, transmits data, and, in some embodiments, may also acquire and amplify two channels of electromyogram (EMG) (not shown). Preferably, it is controlled by firmware in an Analog Devices ADuC7020 processor. The DAQ section samples finger sensor unit data at 128 Hz for each of the six channels. Onboard memory provides 12 hours of data storage. A lithium-based battery provides 12 hours of continuous use and is rechargeable by a computer through a lemo to USB connector cable. The command module 3 also integrates a membrane switch label (not shown) with LED indicators for power and charging (not shown). Three membrane switches inside the label (not shown) provide on/off control and two subject diary inputs. The command module 3 may perform rudimentary signal processing, such as filtering and analog-to-digital conversion, on the movement signals received from the sensor unit 2 before transmitting the movement signals to a receiver unit 5. This transmission may be wired, but is preferably wireless, advantageously providing the subject the greater comfort and convenience of being untethered as well as endowing the system with enhanced safety and portability. The wireless link frees subject motion, which allows unimpeded and accurate assessment of subject symptoms. In operating room, a small untethered system has the added benefits of reducing further subject discomfort and not impeding clinical traffic. A wireless system which is not directly connected to any source of AC power has the added benefit of reducing or eliminating risk of electrical shock. Preferably, the wireless transmission is robust and operates in a frequency band designated for hospital use. Preferably, the radio is a Bluetooth radio operating in the 2.4 GHz band. More preferably, radio transmission occurs over the Wireless Medical Telemetry Service (WMTS), dedicated by the FCC to wireless medical equipment used in hospitals, which comprises the frequencies 608 to 614 MHz, 1395 to 1400 MHz and 1429 to 1432 MHz. Preferably, radio communication is accomplished using a mix of traditional heterodyning techniques along with newer software radio techniques. For example, receiver structure consists of a band select function of either 608-614 MHz or 1395-1432 MHz, followed by a heterodyning operation. The lower frequency band undergoes one frequency translation while the upper undergoes two frequency translations. For the low band (608-614 MHz) the signal is translated to 44 MHz where it is then sampled by an A/D converter and demodulated in the "sampled" domain. The high band is translated first to the lower frequency band (608-614 MHz) and processed in the same fashion. The software radio demodulation approach accommodates many different data rates and modulation formats and advantageously allows future radio upgrades to be implemented simply by changing the signal processing program opposed to necessitating an entire analog hardware redesign. The low band transmit signal is a simple frequency source modulated with appropriate information. For the high band transmit signal, the same signal used for the low band transmit signal is mixed with a high frequency signal to produce the desired output. For transmitter operation, the signal processing hardware generates the modulating signal for all different signal formats and data rates. The signal processing hardware outputs a modulating signal input to an oscillator circuit that creates the modulated transmit signal. The modulated signal, for the high band, uses the low band modulator and translates that signal to the proper operating frequency. Since the modulator is the same for both low and high bands it ensures the same signal quality regardless of operation band. Since the radio is a transceiver (two-way link), the design can serve as a master or slave; thus the same design can be employed in the command module 3 as well as in the receiver unit 5.

Data may also be collected in an on-board memory contained within the command module 3 and downloaded to the tablet computer 6 later, advantageously allowing the subject to wear the sensor unit 2/command module 3 at home for more prolonged symptom monitoring.

The receiver unit 5 may be integrated into some larger system—for example, it may consist of a Bluetooth receiver integrated into a device such as a laptop or tablet computer, a cellular phone, etc.—or it may a separate device built into an enclosure. In the illustrated embodiment, the receiver unit 5 is connected to a tablet computer 6 via one of the USB ports (not shown, in a dongle-style connection that advantageously eliminates a cable), is powered thereby, and comprises a radio frequency transceiver capable of 2-way radio frequency communication with the command module 3. Power regulation and USB-based data transmission protocols may be among any known in the art. The receiver unit 5 may be, in some embodiments, an off-the-shelf Bluetooth USB adapter dongle.

Tablet computer 6 is used to collect data transmitted from the control module 3, allow user inputs to store and track motor performance and therapy device parameter settings, and provide clinicians with real-time symptom quantification feedback. The tablet computer 6 of the illustrated embodiment may be any computing device with a user interface 7, including a smart phone, PDA, laptop computer, desktop computer, iPhone, iPad, or the like. Preferably, the tablet computer 6 is lightweight and portable, allowing for its easy transport within an operating room, and includes a touch screen. In some embodiments, the tablet computer 6 may be equipped with a clip or hanger (not shown) for easy mounting to an operating room pole.

The user interface 7 may be visual, preferably comprising a touch screen, or it may be an audio interface that accepts and transmits spoken commands. The user interface 7 preferably provides several key components and an overall software wrapper. First, it preferably provides a main menu (not shown) to access all software features including a subject database (not shown), the tuning assistant software which runs the therapy device parameter settings tuning algorithm, and software for automatically generating clinical reports following tuning sessions. Next, it preferably provides a module to view real-time motion data transmitted by the sensor unit 2/command module 3, helping ensure proper setup and communication prior to clinical therapy device programming. The user interface 7 also preferably communicates with the system registry to store system parameters and clinician preferred settings. Finally, a help menu (not shown) with troubleshooting guides and frequently asked questions is preferably included.

Subject data management is an important aspect of clinically-used embodiments of the present invention. Preferably, the format of the software used with the system is designed for a high volume subject database. Any database known in the art may be used but is preferably one which scales well to accommodate thousands or tens of thousands of subjects. Preferably, the database has fields for subject history, including the subject's surgery dates, a running list of the subject's clinical sessions (past and/or future scheduled), the subject's primary physician, neurologist, medication dosage, etc. Preferably, the subject is also programmed with the ability to import e-mails and other documents into the subject history, and to export a standardized patient information sheet (reporting). Preferably, the database is programmed so as to permit all stored subject information to conform HIPPA guidelines for patient privacy and confidentiality.

A programmer unit 8 is used by the clinician to program the subject's therapy device, that is, to adjust the therapy device's parameter settings.

Alternatively, the sensor unit 2 may transmit to a server or group of servers such as with cloud computing whereby the data resides on such server or group of servers and can be accessed at the point of testing or some remote location for review by a clinician or doctor. In all exchange of information that occurs in the above example and in all other embodiments of the present invention, it is important that information be exchanged securely and in ways that do not improperly disclose a subject's identity. Because of this, in certain preferred embodiments, all personal information of a subject is stored securely at a remote database and is accessible only through a secure network connection wherein both the database and connection protocol are compliant with standards required by the health insurance portability and accountability act (HIPAA). Often, this will require encryption of the data to eliminate the possibility that the data can be read by a third party and many preferred embodiments of the present invention include the use of data encryption.

As indicated in the above example, various embodiments of the present invention can involve sending a movement disorder monitoring device home or to another remote location with a subject to be used for movement disorder testing away from a physician's or clinician's place of practice. Once the subject arrives home, the movement disorder monitoring device is placed in the subject's home where it may be powered by either a single or multiple on-board batteries or by another power source in the subject's home such as a standard 120 volt alternating current outlet. Once in the home a display unit may, at intermittent times selected by the programming physician or clinician, alert the subject of the need to perform certain movement disorder evaluation tasks. At these times, the display unit may produce a sound, provide a visual alert on its display screen, or a combination of both as a way to alert the subject. In response to the alert the subject will place at least one sensor on his or her extremity(ies) as instructed by the display unit and will proceed to follow other instructions provided regarding how to properly complete certain tasks used to evaluate the severity of the subject's movement disorder symptoms. In certain embodiments, the subject may be video recorded by the camera of the display unit so that a physician can at a later time verify that the tasks were indeed correctly completed. Preferably, the subject will also answer other questions at this time regarding a subject's self-assessment of his or her symptoms and the subject's adherence to and use of treatments prescribed by the subject's physician or another clinician. Such questions may consist of inquiries related to the subject's perception of the present severity of the subject's symptoms, the subject's most recent dose of pharmaceutically-based treatment, the subject's activity level throughout the day, and other similar pertinent information that is desired to be known by the physician to help better understand a subject's symptoms. As noted above, however, in certain other embodiments, the display unit may not be programmed to alert a subject, but instead may simply be left available for a subject to input data regarding his or her symptoms or to select movement disorder assessment tasks to perform from among various options according to the subject's personal preferences and schedule as well as the subject's own subjective view of the severity of his or her symptoms.

By way of a more specific example of the above situation, a physician or other clinician may see a subject for treatment of PD or other movement disorders and the subject may indicate to the physician that his or her symptoms associated with PD or other movement disorders vary greatly throughout the day. To better understand the diurnal fluctuations of the subject's symptoms and to be better able to tune the movement disorder therapy device, the physician may program a display unit to intermittently alarm over a certain duration of time and to instruct the subject to, for example, wear the sensor on the subject's right hand while performing hand grasping exercises, finger tapping exercises and to simply wear the sensor for a period of time while resting to examine the severity of a subject's rest tremor.

Figure 3:
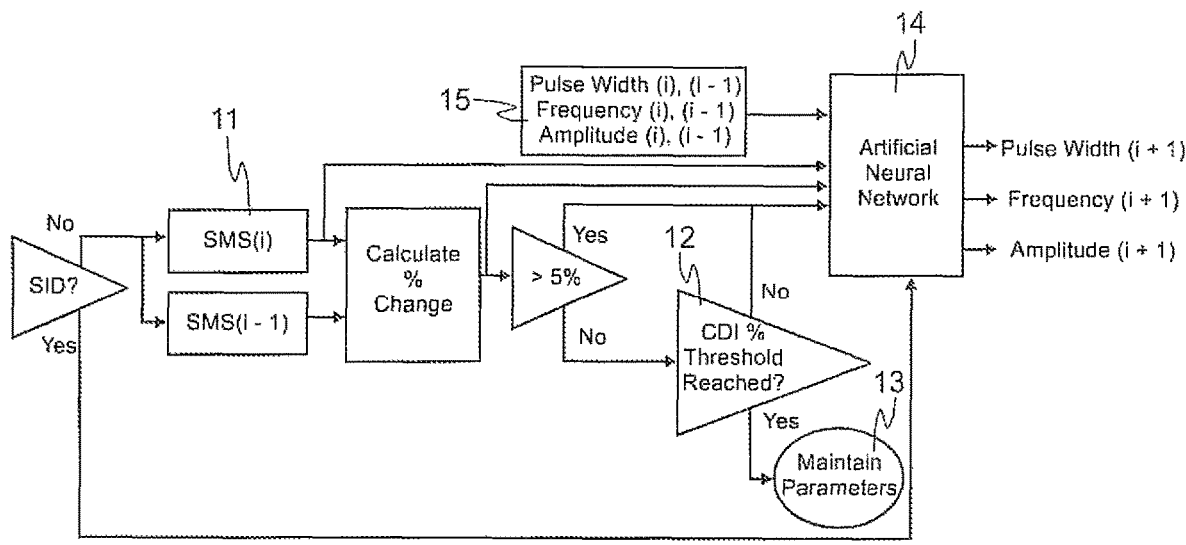
FIG. 3. Flow diagram of the parameter adjustment suggestion algorithm in some embodiments of the present invention.

In the embodiment illustrated in FIG. 1, the subject 1 performs a movement disorder test according to instructions. Optionally, these instructions may be provided by an instructional video clip displayed on a the user interface 7 of the tablet computer 6, advantageously providing the subject with a standardized visual aid to mirror while a test is conducted and data is collected. Such a system implemented in software and provided through user interface 7 ensures the same clinical examination protocol is used subsequent office visits, advantageously allowing clinicians to more repeatedly and objectively track symptoms and assuring inter-subject data correspondence. Alternately, the subject 1 may simply follow instructions given by a clinician. Preferably, testing includes (or may be limited to) three types of tremor tasks (resting, postural, and kinetic) and three types of bradykinesia tasks (finger tapping, hand grasps, and pronation/supination). Either alternatively or in addition, testing may include various gait/balance tasks as well. The sensor unit 2 collects data which is sent to command module 3 for transmission via radio link to a receiver unit 5. The processor of the tablet computer 6 processes the movement data to extract kinematic features which are then fed into a trained algorithm implemented as a software algorithm in the tablet computer 6. The trained algorithm may output a score which may then be displayed on the user interface 7. The processor of tablet computer 6 then computes suggested therapy device parameter settings based at least in part upon the current therapy device parameter settings and the collected movement data and/or the quantified score computed therefrom. An exemplary tuning algorithm for computing the suggested therapy device parameter settings is illustrated in FIG. 3. The clinician may input the existing therapy device parameter settings into the user interface 7, or the tablet computer 6 may communicate directly with the programmer unit 8, wired or wirelessly, to ascertain preexisting parameter settings.

Once suggested parameter settings adjustments are computed by the tuning algorithm, the adjustments or new settings are displayed on the user interface 7. They may then be manually entered into the programmer unit 7 for reprogramming of the therapy device, or the tablet computer 6 may communicate directly with the programmer unit 8, wired or wirelessly, to adjust the parameter settings.

The therapy device may be reprogrammed wired or wirelessly, and typical implanted therapy devices are enabled with means of wireless transcutaneous reprogramming.

Figure 2:
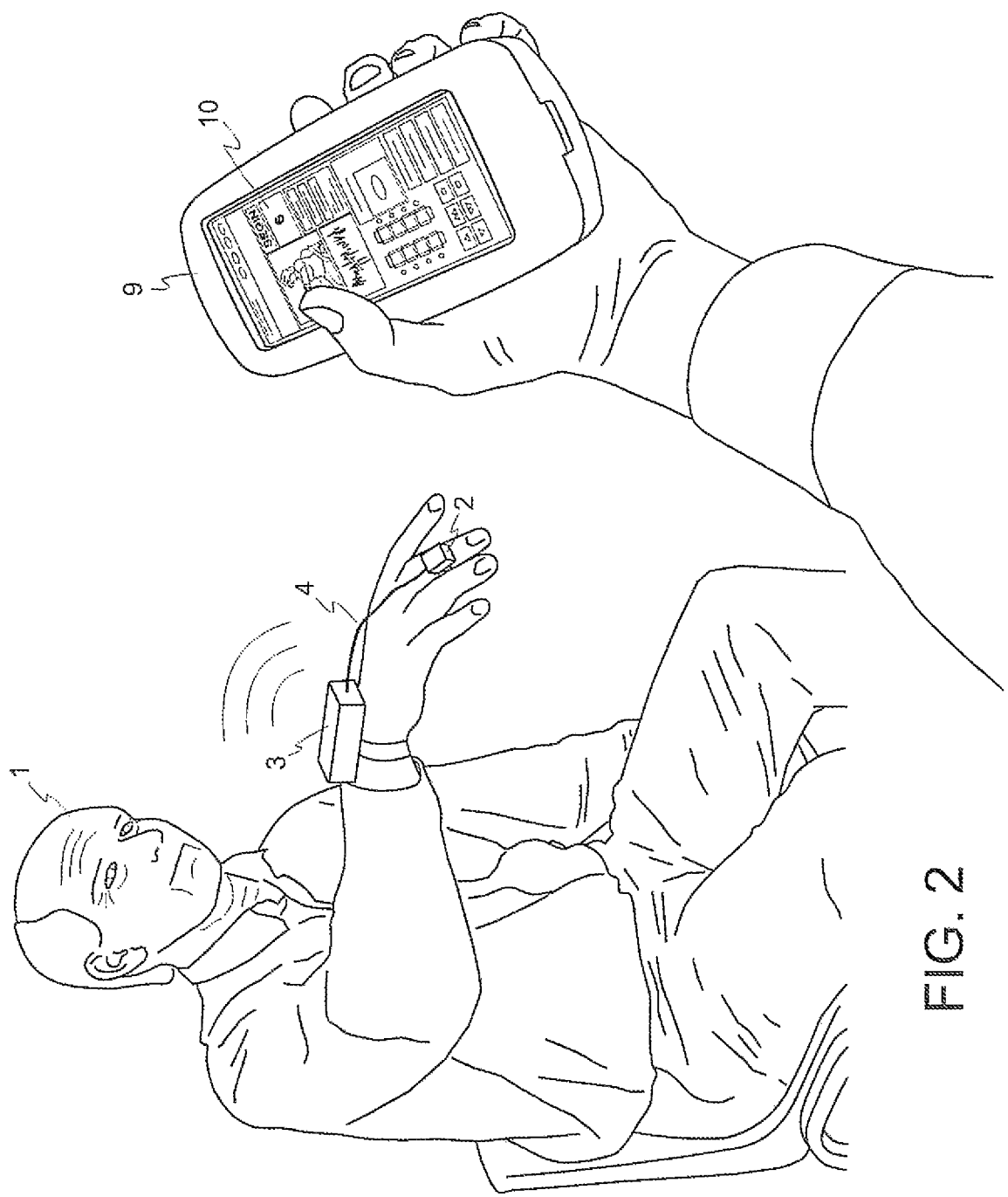
FIG. 2. Schematic view of a subject undergoing post-surgical DBS adjustment with another embodiment of the invention.

The alternate embodiment of the invention depicted in FIG. 2 advantageously combines the receiver unit 5, the tablet computer 6, the user interface 7, and the programming unit 8 into one clinician unit 9 having improved user interface 10, which is preferably a touch-screen interface. The command module 3 transmits movement data acquired by the sensor unit 2, as described above, to the clinician unit 9, where the movement data is analyzed and parameter settings adjustments are computed. The parameter settings may then be automatically or semi-automatically updated, with the clinician unit 9 interfacing with the therapy device (not shown) directly to reprogram the therapy device's parameter settings. In the case of a semi-automatic update of parameter settings, the improved user interface 10 provides a prompt, which may consist of, for example, a button or an audio query. Response to the prompt (e.g., pressing the button or giving a vocal command) initiates the therapy device reprogramming.

Preferably, the touch screens of tablet computer 6 and clinician unit 9 permit the clinician to interact with the user interface 7 or the improved user interface 10 using a large sterile stylus (not shown).

In alternate embodiments of the invention, quantification of movement disorder symptoms may be performed using a different form of movement measuring apparatus. In one such example, a webcam built into the tablet computer 6 or clinician unit 9, or a video camera or set of multiple cameras connected thereto, view the subject 1 performing the motion disorder test and feed video data into the tablet computer 6 or clinician unit 9 where, for example, machine vision algorithms measure the motion of the limbs of the subject with respect to time according to any method known in the art. Such a method may consist, for example, in determining marker points along the limb of the subject in order to gauge relative motion, and such a method may be assisted by applying more visible markers (not shown) on various points on the limb of a subject 1, such as is common with motion capture technology. In such case, the need for sensor unit 2, with its accelerometers and gyroscopes, may be obviated.

In a preferred embodiment, a programming session will be carried out according to a protocol comprising the following steps. The clinician will asses all motor task baseline scores. The clinician will check electrode impedance for wire damage. The clinician will record medication dosages, which information preferably includes information relevant to the subject's present level of medication, such as time and dosage of last medication administration. The clinician will select programming motor tasks, and in conjunction with the programmer unit 8, 9, the subject will repeat the series of motor tasks for each stimulation setting. The clinician will then enter the DB S settings and corresponding scores for each chosen motor task, with the ability to switch between tasks for entering data and selecting which DBS parameters are fixed: frequency, current, pulse width, and contact setup (mono, bi, tripolar). Finally, the clinician will assess all motor tasks post-programming. Preferably, the system will provide the ability to enter DBS settings and scores completely either with a finger or stylus on a touch screen, and/or with a mouse and/or with a keypad or keyboard using the tab key to switch between data input fields. Preferably, the system provides three data input modes: (1) enter stimulation and score information, click update, enter next measurement; (2) enter information and display updated tuning map; (3) use stylus/finger/mouse to click on the tuning map for the appropriate measurement, with a new input box appearing to enter score/side effects/notes.

It is advantageous in some embodiments for the system to permit the clinician performing the programming session to enter a large number of variables in order to provide a complete assessment of the DBS tuning. The following is a representative list of information which may be entered in each programming session: (1) general subject information, including patient ID, whether the subject's DBS implant is unilateral or bilateral, implant electrode site location and side; (2) motor tasks performed during tuning, including (a) tremor: rest, postural, kinetic, (b) bradykinesia: finger tap, hand grasp, pronate/supinate, (c) rigidity: elbow/knee, head/neck, (d) leg agility: heel tapping, (e) rising from chair: with arms crossed, (f) posture, (g) gait: walking quality, (h) postural stability: pull back; (3) motor scores, in the form of integer scoring from 0 (no severity) to 4 (extremely debilitating); (4) DBS settings, including (a) contact: cathode/anode, monopolar (case (battery pack)+, 0 to 3 neg)/bipolar, contact 0 is the deepest, (b) stimulation parameters including amplitude (in volts), frequency (in Hz), current (in amps), pulse width (in microseconds), (c) side effects and/or capsule effects, including (i) motor effects, such as worsening of symptoms, dyskinesias, facial pulling, (ii) non-motor effects, such as blurry vision, soft or slurred speech, sweating, headache, tingling (transient/non-transient), fatigue, sense of euphoria, (iii) new or atypical side effects and update list of notable effects Details of the process of movement disorder symptom score calculation are described in this application's parent application, U.S. patent application Ser. No. 12/250,792, which is herein incorporated by reference.

FIG. 3 shows an example tuning algorithm used for computing suggested parameter settings adjustments. This basic algorithm utilizes symptom severity data, detected stimulation induced dyskinesias (SID), and clinical inputs such as clinician defined improvement percentage (CDI %) to compute suggested stimulation parameter settings. Based on the typical clinical description, several constraints reduce the number of degrees of freedom in the tuning algorithm. During DBS programming, the clinician may utilize any subset of the motor task mentioned previously to evaluate motor performance. The average tremor score (ATS) is computed for the set of tremor tasks and the average bradykinesia score (ABS) is computed for the set of bradykinesia tasks utilized by the clinician for a given iteration. This reduces the number of symptom severity outputs from a maximum of three to one for each symptom. Dyskinesia is either "on" or "off."

Recording symptom severity before the therapeutic device is turned on obtains baseline. In the case of DBS adjustment, before utilizing the tuning algorithm, the best monopolar electrode contact is determined by finding the contact that provides the largest therapeutic width, i.e., the largest change in supplied voltage from when a clinical benefit is noticed to when side effects occur. This is accomplished by fixing stimulation pulse width to 60 μs, frequency to 130 Hz, selecting one contact, and then stepping the voltage amplitude in small increments of approximately 0.2 V. The procedure is repeated for each contact. The contact that provides the largest therapeutic width is selected. With the pulse width (60 μs) and frequency (130 Hz) set to typical values, the clinician then sets the amplitude to the lowest voltage that provides a significant decrease in symptoms. If a satisfactory result is not achieved, pulse width or frequency may also be increased. This can be a time consuming iterative process that must be completed several times over the first few months as microlesioning heals and requires a compensatory increase in stimulation amplitude to maintain clinical benefit. In various embodiments, the invention includes a sensitive tool, implemented in software and accessed through user interface 7 or improved user interface 10 to detect the instant of clinical benefit as voltage amplitude is increased and the instant any stimulation induced dyskinesias are detected. Use of the invention as a sensitive measure of clinical benefit onset and side effect occurrence advantageously ensures the contact with the greatest therapeutic width is selected.

Once the contact width is selected, the initial parameter settings adjustment iteration may be completed with literature-defined settings of 60 μs and 130 Hz stimulation. Amplitude is set to 0.2 V initially, then modified by the clinician in subsequent iterations. After each stimulation parameter change, the clinician uses the user interface 7 or the improved user interface 10 and guides the subject through motor tasks. The tuning algorithm output provides a suggested parameter direction output after each motor task evaluation by utilizing the movement disorder quantification algorithm. The invention thereby maximizes clinical benefit by minimizing tremor and bradykinesia, minimizes adverse effects of stimulation-induced dyskinesias, and minimizes current consumption to maximize battery life. Thus, one objective function is to minimize the sum of average tremor score (ATS) and average bradykinesia score (ABS), known as the summed motor score (SMS) 11. This objective is achieved in the tuning algorithm by continuing to increase stimulation in the same direction as long as SMS is decreasing. A higher SMS corresponds to worse motor symptoms. A second constraint is that stimulation induced dyskinesias (SID) should not occur. If they are detected, the direction of the parameter change is reversed. Another system constraint is the minimization current consumption. This is accomplished by allowing a clinician defined improvement percentage (CDI %) 12 and considering any changes of less than 5% in SMS to be insignificant. When these conditions are met, the current parameter level is maintained 13 due to the SMS goal being achieved and with consideration given to diminishing clinical returns, in order to maximize battery life. Once optimized amplitude has been achieved or reaches 3.6 V, the clinician may adjust pulse width or frequency utilizing the same algorithm. The chances of the feedback system settling into local minimums are reduced by ensuring several of the settings are set at clinically accepted levels for the initial iteration and making only moderate adjustments as required.

While manual DBS programming frequently entails stepping through small incremental changes, this process can be wastefully time-consuming if the motor symptom response of the subject indicates larger changes are required. The implementation of an artificial neural network 14 to output suggested stimulation parameters minimizes programming iterations to reduce surgical and outpatient tuning session time.

Preferably, the artificial neural network 14 used in the tuning algorithm used by some embodiments of the present invention is trained with recorded clinician-made stimulator parameter changes in response to motor symptom severity changes during stimulator programming to minimize required iterations while still utilizing objective symptom severity measures to optimize performance. In this way, the algorithm takes clinician experience into account. Experienced clinicians are generally successful in quickly reducing the number of potentially successful parameter settings for tuning DBS systems. An expert clinician is capable of recognizing severe motor symptoms and modifying a parameter by a larger magnitude, then when the symptom is less and only fine-tuning is required. The present invention is therefore capable of quantitatively detecting motor symptom severity and suggesting a parameter change that approximates or mirrors the parameter change that would be made by an expert clinician.

Artificial neural network 14 may be implemented, for example, with the MATLAB Neural Network Toolbox offline using resilient backpropagation batch training. Inputs to the neural network may include current and previous stimulation settings 15 and motor responses.

Figure 4:
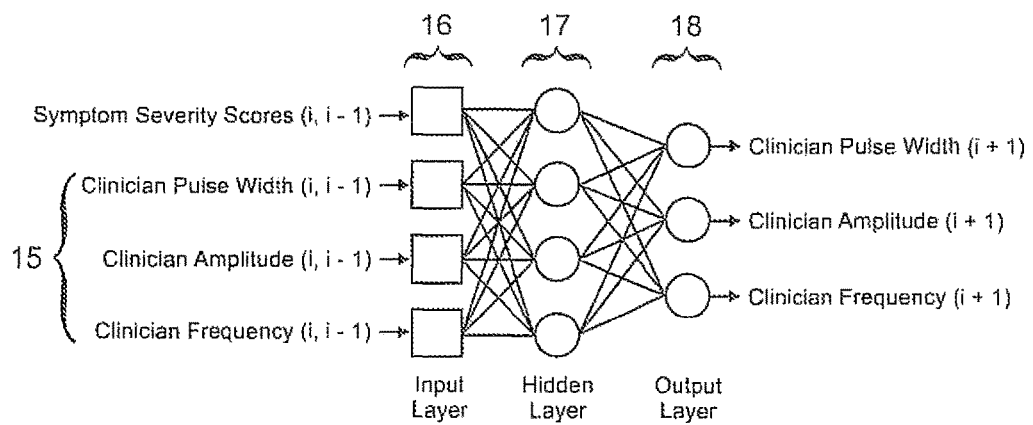
FIG. 4. Flow diagram of the artificial neural network of the parameter adjustment suggestion algorithm in some embodiments of the present invention.

FIG. 4 illustrates a two-layer network structure consisting of one hidden layer 17 with four neurons using "tansig" transfer functions and one output layer 18. As neural networks may fall into local minimums when being trained, each network is preferably trained three times with randomized initial weights and biases and the best training results are selected. Additionally, early stopping improves network generalization. Data is separated into training and generalization sets to ensure trained networks produce accurate results both when the training set is reapplied and also when it is generalized to new data. Preferably, training data is collected from multiple patients. To ensure that the system generalizes to new patients, network generalization can be tested by training the system using a jackknife "one left out" method. Using such a method, the neural network is trained using data from, for example, only nine of ten subjects. Data from the nine subjects in the training set is then reapplied to the trained network to ensure good correlations while data from the "left out" subject is used to test generalization. The method is repeated, leaving out each subject one time. For each training and generalization set, both the mean squared error (MSE) and R-squared values between the clinician-made stimulator parameter changes and those output by the system for each stimulation parameter are calculated. The MSE and R-squared for all training and generalization sets are averaged. Preferably, the system achieves normalized MSE values of less than 10% and R-squared values of greater than 0.8 to show substantial agreement between system-suggested simulation parameter changes and clinician-made stimulation parameter changes.

Preferably, separate data sets and acquired, and separate neural networks are trained, for the surgical and outpatient scenarios. Preferably, the data used to train the algorithm averages the experience of multiple expert clinician programmers.

Preferably, the tuning algorithm comprises a neural network as illustrated in FIG. 3, but it might instead or in addition comprise one or more of adaptive continuous learning algorithms, linear quadratic Gaussian control, Kalman filtering, and model predictive control.

When the tablet computer 6 is connected to the Internet or similar communications network, wired or wirelessly, it may therefore transmit subject data to remote systems, allowing general practitioners to conduct DBS programming remotely, minimizing travel for a subject 1 who lives far from a DBS implantation center or suitable programming clinic, so long as the subject 1 is equipped with the sensor unit 2/command module 3 and means of programming and/or making parameter settings adjustments to his or her therapy device (including DBS implant).

Figure 5:
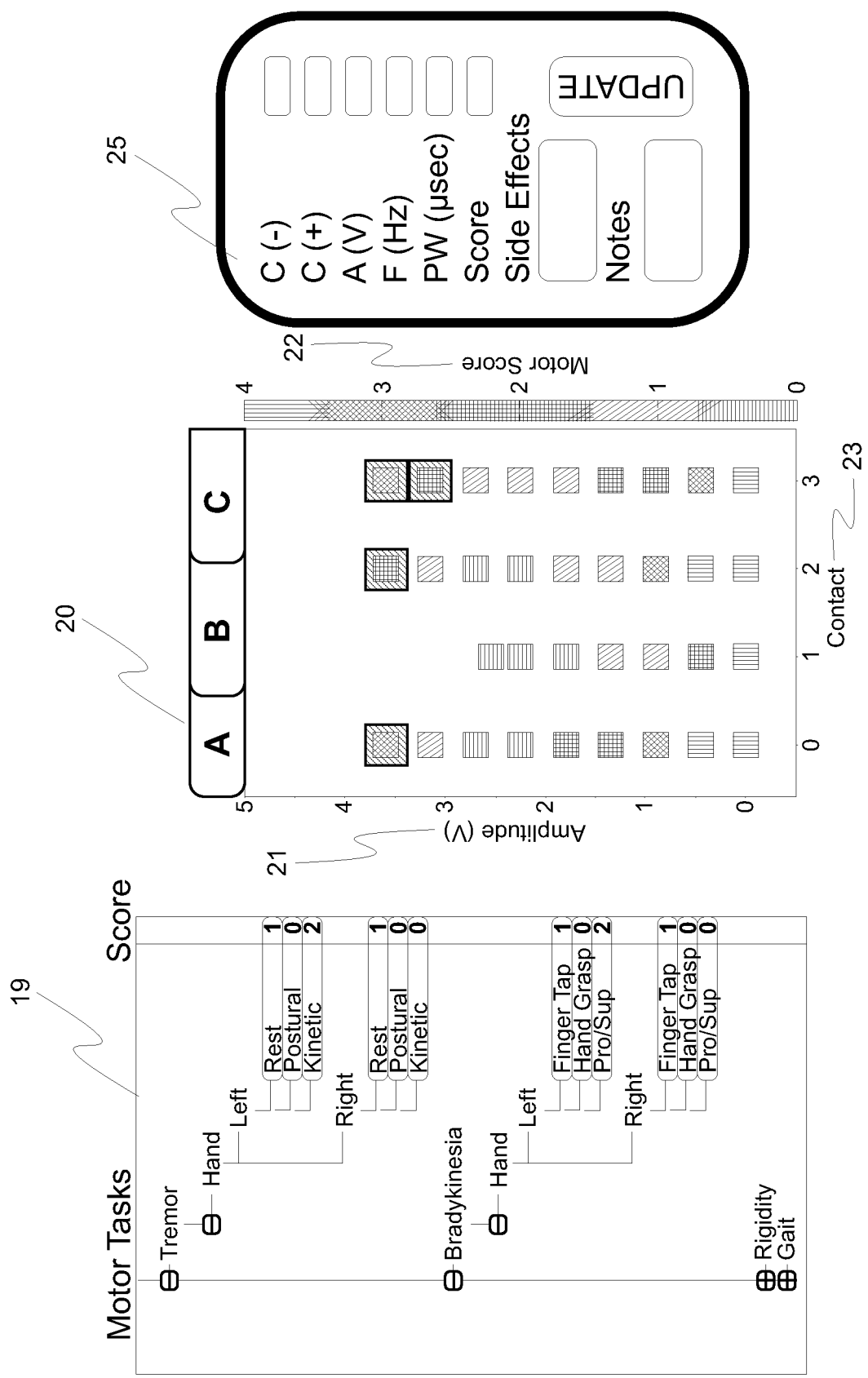
FIG. 5. Graphic depiction of display pages displaying test results and scores, as well as a possible parameter input screen.

FIG. 5 depicts a series specific display pages corresponding to reporting score provided in various embodiments of the present invention. These examples of methods of reporting scores with visual displays associated with each display stage of the test process are merely exemplary. One example of a displaying a score is the expandable menu view 19, where the user (i.e., clinician, physician, or patient performing self-testing away from the clinician) is presented with a list of the different types of movement disorders or movement disorder symptoms which may or may not have been measured in a given test. In the portrayed example of this expandable menu view 19, the movement disorder symptoms that may be selected include tremor, bradykinesia, rigidity and gait. The user is then given the option of expanding the results for each of those movement disorders or movement disorder symptoms through a series of levels (i.e., hand then to left or right), in order to view the score that was determined for each particular disorder or symptom in the indicated portion of the subject's body. By way of clarification and example, the subject shown in menu view 19 received a score of 1 during rest for the symptom of tremor in the left hand, and a 2 for the pronation/suppination task for bradykinesia in the left hand.

Another display method, which may be independent or used in conjunction with the expandable menu view is the tuning map 20. A tuning map 20 is generated for each task that the subject is directed to perform and depicts the severity of the symptoms measured in each sensor that is used for the given task. Each task that is performed is represented on a different tab (i.e., tab A, tab B, tab C). The amplitude 21 at which the test was performed is measured in volts and indicated on one vertical axis of the tuning map 20. The calculated or estimated score 22 is depicted on a vertical axis of the tuning map 20 as well. Each individual box that is shown represents a test performed 24. Preferably, the tuning map 20 is shown on a color display (not shown) and the severity of the symptom is indicated not by color. In this drawing, the colors are represented by different types of shading or cross-hatching. Each column in the tuning map 20 represents a different contact on the DBS probe. Therefore, each individual test box 24 depicts the results of performing a task while administering DBS at a prescribed voltage amplitude 21 and provides both a severity of the symptom which was detected or measured by virtue of the color (represented by the cross-hatching) which also correlates to a given motor score. Additionally, each individual test box 24 may be selected, for example by pressing it on a touch-screen device, as representing by the test boxes 24 which are outlined in black. When a test box 24 is selected, the user is able to see a detailed view (not shown) of the statistics and parameters of the test corresponding to that box.

A variable window 25 may display on the unit as well which allows the user to input various conditions that have an effect on the test and test results. These variables are calculated into the test results and help to give a more accurate calculated symptom score.

Figure 6:
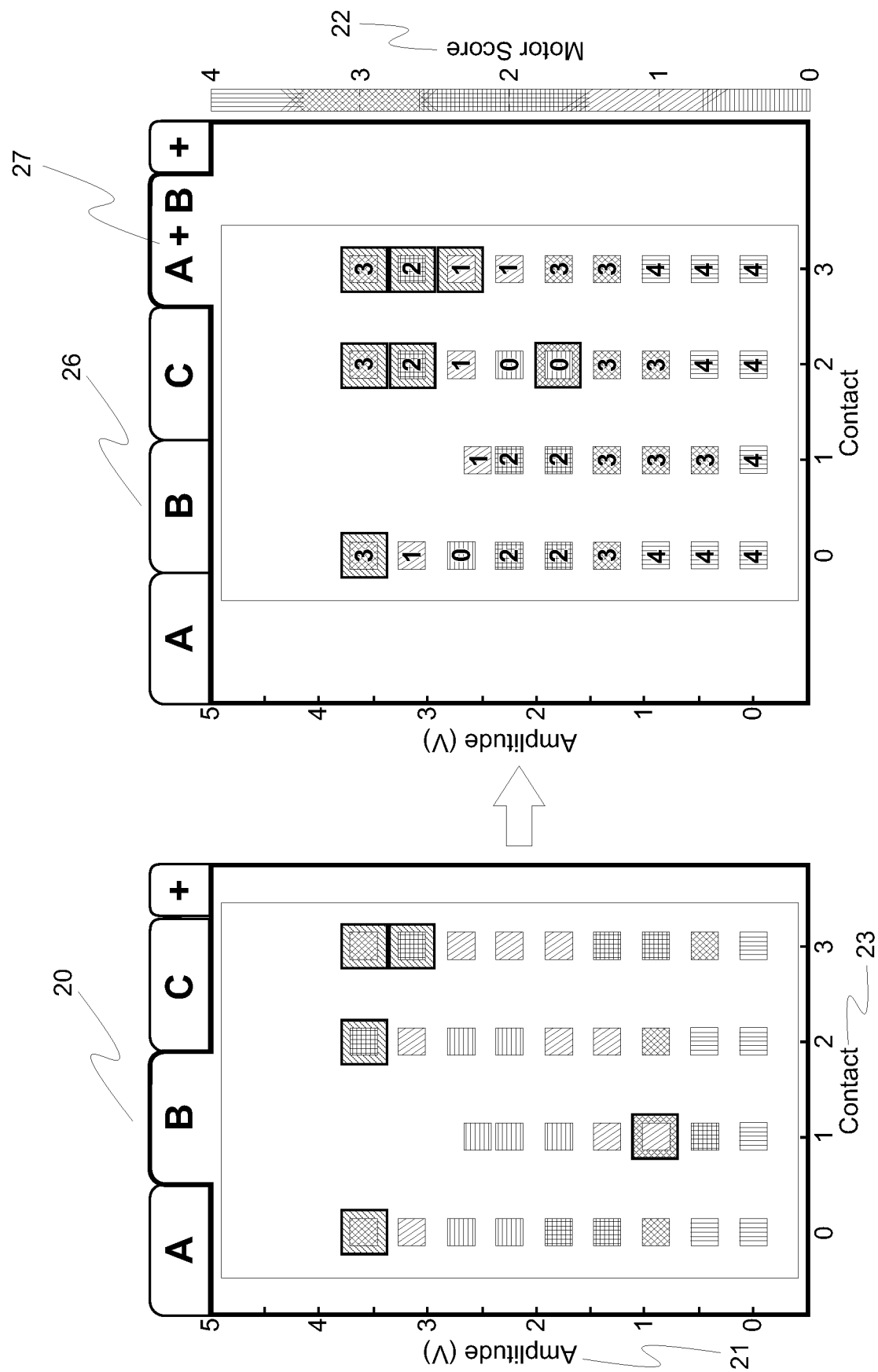
FIG. 6. Graphic depiction of tuning maps used to display test results and symptom severity measured by the system.

FIG. 6 portrays the tuning maps 20 in greater detail. Each task performed is represented again by a separate tab with its own tuning map 20. The amplitude 21 of the voltage at which the test was performed is tracked along one vertical axis of the map 20 for each contact 23 on the DBS lead, while the severity of the symptom detected or measured is displayed as a score 22 and correlated to a color of each individual test ox 24. The right side 26 of FIG. 6 portrays a new tab 27 which represents the combination of tabs A and B. This combination tab 27 represents the combination of the tuning maps for tasks A and B.

The combination 27 is a result of the user selecting those two tuning maps to be combined together in some mathematical way (i.e., averaging) in order to show the results of how the scores for each task combine in order to optimize the DBS level for treating the subject. In other words, the goal is to minimize the voltage at which the DBS is to be supplied while simultaneously minimizing the severity of the subject's symptoms. Combining the tuning maps for each task allows the user to see a resulting score and select the DBS test parameters which are as close to optimal as possible. It is also conceivable that the system would be designed to be a closed-loop system, (i.e., for an implanted home-diagnostic and therapeutic device) which would not require extensive, or any, user input, but would perform the optimization automatically.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A system for adjusting the parameters of a deep brain stimulation implant therapy or treatment device for treating a subject's movement disorder by a clinician, the system comprising:
   a deep brain stimulation implant therapy or treatment device with adjustable parameters;
   at least one internal or external sensor for quantifying at least one symptom of a subject's movement disorder, the at least one internal or external sensor adapted to output a signal related to the at least one quantified symptom;
   a command module adapted for receiving the signal acquired by the at least one sensor, the command module comprising a memory and being adapted for processing the signal acquired by the at least one sensor to provide a digital signal corresponding to the at least one quantified motor symptom;
   a clinician unit comprising a processor with a tuning algorithm, the processor adapted in part for receiving and processing the digital signal and for receiving an input related to the subject's therapy or treatment parameter settings in place during measurement of the signal with the at least one sensor, and the tuning algorithm adapted to produce an output comprising computed adjustments for one or more of the adjustable parameters of the deep brain stimulation implant therapy or treatment device, the output being based at least in part on the signal acquired by the at least one sensor and at least in part on the input related to the subject's deep brain stimulation implant's parameter settings; and
   a display for receiving the output.

2. The system of claim 1, wherein the tuning algorithm is an adaptive continuous learning algorithm or a model predictive control algorithm.

3. The system of claim 2, wherein the system comprises at least two sensors for quantifying at least one symptom of a subject's movement disorder including at least movement sensor and at least one physiological signal sensor.

4. The system of claim 2, wherein the clinician unit is a smartphone or tablet computer and the system further comprises an interface adapted for providing the therapy or treatment device with the output.

5. The system of claim 4, wherein the therapy or treatment device is a deep brain stimulation (DBS) device and the at least one adjustable parameter is one or more parameters selected from the group consisting of stimulation frequency, amplitude, current, pulse width, and contact configuration.

6. The system of claim 4, wherein the therapy or treatment device comprises a drug delivery device, and the at least one parameter is one or more of drug dosage amount and drug dosage administration frequency.

7. The system of claim 4, wherein the output is provided to the subject's therapy or treatment device via the interface automatically or upon manual or vocal confirmation of the presented estimated or calculated level of adjustment, the confirmation, if used, being made by a medical professional or the subject.

8. A system for adjusting the parameters of a deep brain stimulation (DBS) device implanted in a subject for treating a subject's movement disorder by a clinician, the system comprising:
   at least one internal or external sensor for quantifying at least one symptom of a subject's movement disorder, the at least one internal or external sensor adapted to output a signal related to the at least one quantified symptom, the subject having a deep brain stimulation implant having a first set of adjustable parameters;
   a command module adapted for receiving the signal acquired by the at least one sensor, the command module comprising a memory and being adapted for processing the signal acquired by the at least one sensor to provide a digital signal corresponding to the at least one quantified motor symptom;
   a clinician unit comprising a processor with a tuning algorithm, the processor adapted in part for receiving and processing the digital signal and for receiving an input related to the first set of adjustable parameters of the DBS device in effect during measurement of the signal with the at least one sensor, and the tuning algorithm adapted to produce an output comprising computed adjustments for one or more of the adjustable parameters of the deep brain stimulation implant, the output being based at least in part on the signal acquired by the at least one sensor and at least in part on the input related to the first set of adjustable parameters of the DBS device;
   a display for receiving the output; and
   an interface adapted for providing the deep brain stimulation implant with the output.

9. The system of claim 8, wherein the tuning algorithm is an adaptive continuous learning algorithm or a model predictive control algorithm.

10. The system of claim 9, wherein the system comprises at least two sensors for quantifying at least one symptom of a subject's movement disorder including at least movement sensor and at least one physiological signal sensor.

11. The system of claim 9, wherein the clinician unit is a smartphone or tablet computer.

12. The system of claim 9, wherein the output is provided to the subject's deep brain stimulation device via the interface automatically or upon manual or vocal confirmation of the presented estimated or calculated level of adjustment, the confirmation, if used, being made by a medical professional or the subject.

13. The system of claim 9, further comprising a closed loop control system adapted for adjusting the at least one adjustable parameter automatically based at least in part on the computed adjustments for the at least one adjustable parameter.

14. The system of claim 9, wherein the output of the clinician unit comprises at least one tuning map depicting optimal DBS lead setting parameters based on the quantified severity of the at least one motor symptom with the tuning map output being in color, shading or cross-hatching on the display.

15. A system for adjusting the parameters of a drug delivery device used with a subject for treating a subject's movement disorder by a clinician, the system comprising:

at least one internal or external sensor for quantifying at least one symptom of a subject's movement disorder, the at least one internal or external sensor adapted to output a signal related to the at least one quantified symptom, the subject having a drug delivery device having a first set of adjustable parameters;

a command module adapted for receiving the signal acquired by the at least one sensor, the command module comprising a memory and being adapted for processing the signal acquired by the at least one sensor to provide a digital signal corresponding to the at least one quantified motor symptom;

a clinician unit comprising a processor with a tuning algorithm, the processor adapted in part for receiving and processing the digital signal and for receiving an input related to the first set of adjustable parameters of the drug delivery device in effect during measurement of the signal with the at least one sensor, and the tuning algorithm adapted to produce an output comprising computed adjustments for one or more of the adjustable parameters of the drug delivery device, the output being based at least in part on the signal acquired by the at least one sensor and at least in part on the first set of adjustable parameters of the drug delivery device;

a display for receiving the output; and an interface adapted for providing the deep brain stimulation implant with the output.

16. The system of claim 15, wherein the tuning algorithm is an adaptive continuous learning algorithm or a model predictive control algorithm.

17. The system of claim 16, wherein the system comprises at least two sensors for quantifying at least one symptom of a subject's movement disorder including at least movement sensor and at least one physiological signal sensor.

18. The system of claim 16, wherein the clinician unit is a smartphone or tablet computer.

19. The system of claim 16, further comprising a closed loop control system adapted for adjusting the at least one adjustable parameter of the drug delivery pump automatically based at least in part on the computed adjustments for the at least one adjustable parameter, and the at least one parameter is one or more of drug dosage amount and drug dosage administration frequency.

20. The system of claim 19, wherein the output is provided to the subject's drug delivery implant via an interface automatically or upon manual or vocal confirmation of the presented estimated or calculated level of adjustment, the confirmation being made, if used, by a medical professional or the subject.

* * * * *